United States Patent [19]
England et al.

[11] Patent Number: 5,264,565
[45] Date of Patent: Nov. 23, 1993

[54] NUCLEIC ACID ENCODING THE $D_2$/M1 CHIMERIC RECEPTOR

[75] Inventors: Bruce P. England, Richmond; Ronald W. Barrett, Sunnyvale, both of Calif.

[73] Assignee: Affymax Technologies, N.V., Curacao, Netherlands

[21] Appl. No.: 645,029

[22] Filed: Jan. 22, 1991

[51] Int. Cl.$^5$ ............... C12P 21/00; C12N 5/00; C07K 3/00; C07H 17/00
[52] U.S. Cl. ............... 536/234; 536/23.1; 536/23.5; 530/350; 530/387.1; 435/240.2; 435/320.1; 435/69.1; 435/69.4
[58] Field of Search ........... 435/6, 4, 70.23, 69.4, 435/69.1, 172.1, 240.2, 320.1; 530/350, 387; 536/27, 28, 29, 23.1, 23.4, 23.5

[56] References Cited

U.S. PATENT DOCUMENTS

4,859,609  8/1989  Dull et al. .

FOREIGN PATENT DOCUMENTS

244221  4/1987  European Pat. Off. .
441483  8/1991  European Pat. Off. .
9112273 8/1991  PCT Int'l Appl. .
9205244 4/1992  PCT Int'l Appl. .

OTHER PUBLICATIONS

Kubo et al., 2 Oct. 1986, Nature 323:416.
Riedel et al., 6 Nov. 1986, Nature 324:68-70.
Allard et al., 1987, Nuc. Acids Res. 15(24):10604.
Peralta et al., 1987, Embo J. 6(13):3923-3929.
Dixon et al., 5 Mar. 1987, Nature 326:73-77.
Strader et al., 5 Dec. 1987, J. Biol. Chem. 262(34):16439-16443.
Kobilka et al., 3 Jun. 1988, Science 240:1310-1316.
Wong et al., 15 Jun. 1988, J. Biol. Chem. 263(17):7925-7928.
O'Dowd et al., 5 Nov. 1988, J. Biol. Chem. 263(31):15985-15992.
Frielle et al., Dec. 1988, Proc. Natl. Acad. Sci (USA) 85:9494-9498.
Kubo et al., Dec. 1988, FEBS Lett. 241(1,2):119-125.
Bunzow et al., 22/29 Dec. 1988, Nature 336:783-787.
Wolf and Kapatos, 1989, Synapse 4:353-370.
Utsumi et al., 15 Sep. 1989, Science 245:1246-1249.
Wess et al., Nov. 1989, FEBS Lett. 258(1):133-136.
Grandy et al., Dec. 1989, Proc. Natl. Acad. Sci. (USA) 86:9762-9766.
Todd et al., Dec. 1989, Proc. Natl. Acad. Sci. (USA) 86:10134-10138.
Giros et al., 21/28 Dec. 1989, Nature 342:923-926.
Monsma et al., 21/28 Dec. 1989, Nature 342:926-929.
Lameh et al., 1990, Pharm. Res. 7(12):1213-1221.
Stormann et al., 1990, Mol. Pharmacol. 37:1-6.
Wess et al., 1990, Mol. Pharmacol. 38:517-523.
Miller et al., 15 Jan. 1990, Biochem. Biophys. Res. Comm. (166(1):109-112.
Albert et al., 5 Feb. 1990, J. Biol. Chem. 265(4):2098-2104.
Cotecchia et al., Apr. 1990, Proc. Natl. Acad. Sci. (USA) 87:2896-2900.
Wong et al., 15 Apr. 1990, J. Biol. Chem. 265(11):6219-6224.
Vallar et al., 25 Jun. 1990, J. Biol. Chem. 265(18):10320-10326.
Palczewski and Benovic, Oct. 1991, TIBS 16:387-391.
England et al., 1991, FEBBS Lett. 279:87-90.
U.S. patent application Ser. No. 241,941 to Bonner et al.

*Primary Examiner*—Robert J. Hill, Jr.
*Assistant Examiner*—Gian P. Wang
*Attorney, Agent, or Firm*—Kevin R. Kaster; William M. Smith; Karen B. Dow

[57] ABSTRACT

Chimeric G-protein linked receptors are constructed which retain ligand binding specificity yet gain the ability to elevate intracellular free calcium as a result of agonist binding. This easily assayed function is provided by the insertion of or replacement with sequences substantially homologous to the i3 loop of a second G-protein-linked receptor. Such receptors are employed, for example, in methods of screening for compounds capable of acting as agonists or antagonists of G-protein-linked receptors.

4 Claims, 3 Drawing Sheets

NUCLEIC ACID ENCODING THE D₂/Ml CHIMERIC RECEPTOR

FIELD OF THE INVENTION

The present invention relates generally to recombinant DNA technology, and more specifically to the construction and use of chimeric G-protein-linked receptors with substantially unaltered pharmacologic specificity and easily assayed reporter functions.

BACKGROUND OF THE INVENTION

Cells receive much of their information through signal transduction pathways that use GTP-binding regulatory proteins (G proteins) to convey signals from cell surface receptors to intracellular effector proteins. When these receptors, called G-protein-linked receptors, bind agonists, they promote the binding of GTP to specific G proteins. GTP binding activates the G protein and thereby allows it to regulate the activities of specific effector proteins.

The effectors regulated by G proteins include enzymes that synthesize cytoplasmic second messengers, ion channels, and transporters. G proteins are thus involved in regulating the synthesis and release of neurotransmitters, the sensitivity of synaptic receptors, general cellular metabolism, cellular differentiation, and growth.

The vital role of G-protein-linked receptors in enabling cells to respond to environmental signals explains their interest to basic researchers who wish to examine more closely their complex interactions with signals impinging upon the cell and with the G proteins which transduce that signal to effector pathways within the cell. It also explains the active interest of the pharmaceutical industry in applying the results of basic research to the development of drugs which interact with G-protein-linked receptors to affect basic cellular processes and treat human disease.

The identification of families of receptor subtypes has increased the need for inexpensive and facile assays for testing large numbers of potential drug candidates. Typically, radioisotopic ligand binding and second messenger assays are employed in screening drug candidates for their interaction with G-protein-linked receptors. These assay methods are difficult and time consuming to perform and involve the use of hazardous and expensive radioisotopes.

Others have proposed the use of chimeric receptors for testing potential drug candidates. This approach was applied to only one class of receptors, those having a single extracellular ligand-binding domain joined to a single intracellular domain which effects a change in the cytoplasm when the receptor binds ligand. In such receptors the two domains are often connected by means of a single highly hydrophobic region which embeds the receptor in a cell membrane. It is a simple matter to fuse the single extracellular region comprising the ligand binding domain to a heterologous reporter polypeptide, thus allegedly achieving useful chimeric proteins which effect an assayable response to ligand binding.

Many other receptors, including G-protein-linked receptors, have a more complex structure. In G-protein-linked receptors, for instance, ligand binding depends upon complex interactions among a number of different domains of the protein, including hydrophobic stretches passing through the membrane. To form chimeric receptors maintaining ligand specificity while effecting an easily assayed response requires a different approach than those previously described.

Thus there exists a need for a method which allows one to easily, cheaply and safely assay ligand binding to G-protein-linked receptors, providing a useful tool for drug discovery efforts, among others. The present invention fulfils these and other needs.

SUMMARY OF THE INVENTION

The present invention provides chimeric G-protein-linked receptor proteins, nucleic acids encoding such proteins, cells expressing such proteins, and methods for employing such proteins for screening for agents which react with such proteins.

The present invention provides chimeric G-protein-linked receptor proteins comprising a first G-protein-linked receptor, which in its native form does not elevate intracellular free calcium ($[Ca^{+2}]_i$) as a result of agonist binding, into which is inserted a G-protein-coupling polypeptide substantially homologous to an i3 loop of a second G-protein-linked receptor. Alternatively and preferably, said G-protein-coupling polypeptide replaces portions of a G-protein-linked receptor (of a different class). In either case, said G-protein-coupling polypeptide is capable of inducing an increase in intracellular free calcium levels ($[Ca^{+2}]_i$) when an agonist binds to said chimeric G-protein-linked receptor Typically, an entire i3 loop of a first G-protein-linked receptor is replaced with said G-protein-coupling polypeptide, which itself is typically substantially homologous to an entire i3 loop of a second G-protein-linked receptor.

The present invention embraces nucleic acids comprising sequences encoding said chimeric G-protein-linked receptor proteins. Such a nucleic acid will typically be an expression vector having a promoter operably linked to a sequence encoding such a chimeric G-protein-linked receptor protein. The present invention further embraces cells into which such nucleic acids have been introduced, normally expression vectors capable of expressing chimeric G-protein-linked receptors in such cells. These cells will typically be mammalian cells.

Finally, the present invention provides a method of screening for agents reacting with such G-protein-linked receptors, comprising the steps of:
  (a) mixing an agent with a cell expressing such a chimeric G-protein-linked receptor; and
  (b) measuring changes in intracellular free calcium. Alternatively, one may also allow an agonist to bind to such a chimeric G-protein-linked receptor after mixing said agent. Most preferably, one measures changes in $[Ca^{+2}]_i$ by means of a fluorescence indicator, such as Fura-2.

BRIEF DESCRIPTION OF THE FIGURES

FIG. 3A. Dopamine (1 mM final concentration) was added to CHO cells expressing $D_{2(414)}$ receptors at the indicated time.

FIG. 3B. Various concentrations of dopamine were added at the time indicated to CHO cells expressing $D_2$/ml receptors. The final concentrations of dopamine from the bottom to the top curve were 0.1, 1, 10, 100, 1000 μM.

FIG. 3C. CHO cells expressing $D_2$/ml receptors were pre-incubated with or without 10 μM fluphenazine for 2 minutes followed by addition of 10 μM dopamine at the indicated time.

DETAILED DESCRIPTION OF THE PREFERRED EMBODIMENTS

OUTLINE

Figure 1:
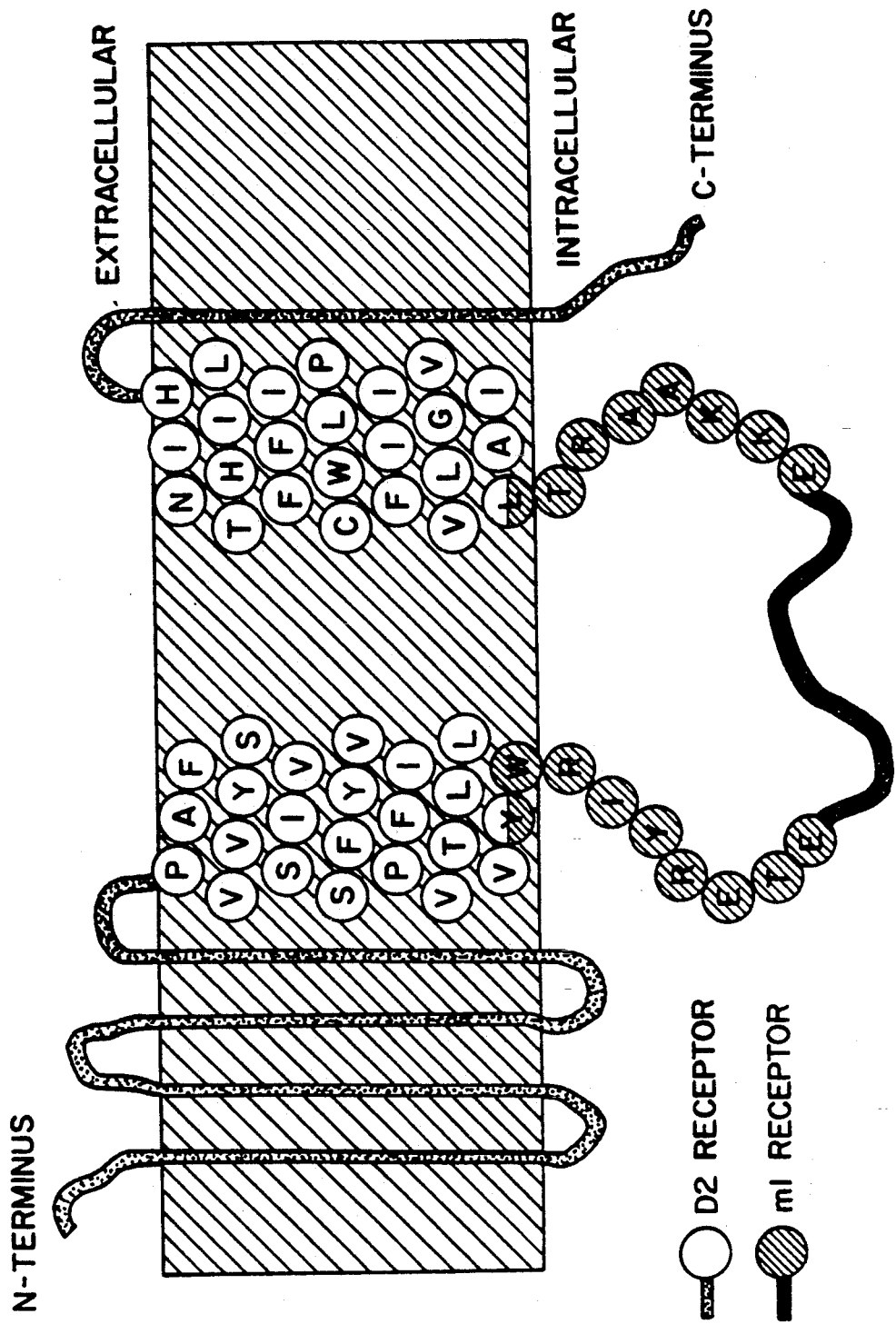
FIG. 1. Structure of the D₂/ml chimeric receptor (SEQ. ID No. 7). The portion of the receptor derived from the D₂(414) receptor is indicated by the grey line and open circles. The portion derived from the ml receptor is indicated by the black line and filled circles. The amino acid residues at the chimera junctions (half-filled circles) were common to both sequences.

I. General description
  A. Structural features of G-protein-linked receptors
  B. Functional features
    1. Ligand binding
    2. G-protein regulatory domains
    3. Effectors
II. Polypeptides
III. Nucleic acids
IV. Methods for use The chimeric receptor of this invention provides a generic strategy for making members of the G-protein-linked receptor family elevate intracellular free calcium ($[Ca^{+2}]_i$) if they do not do so in their native form. Such an approach will be an important tool in screening methods for identifying drugs which interact with G-protein-linked receptors.

If the nucleotide sequence of a receptor is known, chimeric receptors can be created quite easily using commonly used techniques. The $[Ca^{+2}]_i$ response, monitored by a fluorescence indicator, is rapid and robust. Thus, with appropriate automation of the calcium assay, it may be possible to accurately and reproducibly screen large numbers of compounds as agonists or antagonists of any previously cloned member of the G-protein-linked receptor family and avoid the hazards and costs associated with the use of radioisotopes. Among other benefits resulting from this invention will be the dramatic acceleration in our understanding of the function of these receptors and the development of therapies for important human diseases.

I. General Description

The G-protein-linked receptors are cell surface receptors which play a vital role in a cell's response to various environmental signals. After binding a ligand, they interact with specific G proteins, which subsequently regulate the activities of specific effector proteins. In this way, signal reception by G-protein-linked receptors amplifies the signal and causes a cascade of intracellular events which ultimately leads to a cellular response (for reviews of G proteins and G-protein-linked receptors, see L. Stryer and H. Bourne, *Ann. Rev. Cell Biol.* 2:391 (1986); A. Gilman, *Ann. Rev. Biochem.* 56:615 (1987); H. Dohlman et al., *Biochemistry* 26:2657 (1987); E. Ross, *Neuron* 3:141 (1989), all of which are incorporated herein by reference). They form in this way the basis of a complex information processing network in the plasma membrane of cells, organizing the signals they receive from multiple receptors and directing them to an appropriate array of effectors. The notable advantage of G proteins as signal transducers is their ability to direct incoming signals from multiple receptors to a large array of cytoplasmic second messenger pathways. A single G protein can integrate signals from a number of different receptors to stimulate a single second messenger pathway, or one or more G proteins can direct information from a single receptor to several different effector systems. They can also balance stimulatory and inhibitory signals to yield a modulated effect. By these complex interactions, G proteins and the receptors with which they interact can coordinate a cell's responses to multiple signals in its environment.

It is likely that more than 100 receptors communicate through G proteins. cDNA's and/or genes for many of these receptors have been cloned, and their structure examined G-protein-linked receptors are a large family of cell surface receptors which includes: the adrenergic receptors, which mediate the physiological effects of catecholamines; rhodopsin and the visual color opsins; the muscarinic cholinergic receptors, GABA-B receptor, and many other neuromodulator receptors, including those for serotonin and dopamine, and receptors for peptide hormones and most eicosanoids. Examples of physiological processes mediated by G-protein-linked receptors are given in Table 1 below.

A. Structure of G-protein-linked receptors

General descriptions of protein structure and its relationship to nucleic acid sequences are discussed in J. D. Watson et al., *Molecular Biology of the Gene*, 4th Ed., vol. 1 and 2, Benjamin/Cummings, Menlo Park, Calif. (1987); and B. Alberts et al., *Molecular Biology of the Cell*, 2nd Ed., Garland, New York (1989), all of which are hereby incorporated herein by reference. A G-protein-linked receptor is a protein either derived from a natural G-protein-linked receptor gene, or which shares significant structural characteristics peculiar to a naturally occurring G-protein-linked receptor.

Receptors are proteins located on cell membranes that perform a signal transducing function, also called activation. Many receptors are located on the outer cell membrane. A ligand binds to the extracellular ligand binding domain in such a way that the conformation of the receptor molecule changes within the cytoplasmic region. This conformational change modifies the effect of the receptor on cytoplasmic components.

TABLE 1

| | EXAMPLES OF PHYSIOLOGICAL PROCESSES MEDIATED BY G PROTEINS | | | | |
|---|---|---|---|---|---|
| Stimulus | Receptor | G protein[a] | Effector | Physiological Response | Reference |
| Epinephrine | β-Andrenergic receptor | $G_s$ | Adenylate cyclase | Glycogen breakdown | Ross & Gilman 1980 |
| Serotonin | Serotonin receptor | $G_s$ | Adenylate cyclase | Behavioral sensitization and learning in Aplysia | Siegelbaum et al. 1982 |
| Light | Rhodopsin | Transducin | cGMP phosphodiesterase | Visual excitation | Stryer 1986 |
| IgE-antigen complexes | Mast cell IgE receptor | $G_{PLC}$ | Phospholipase C | Secretion | Smith et al. 1985 Nakamura & Ui 1985 |

TABLE 1-continued

EXAMPLES OF PHYSIOLOGICAL PROCESSES MEDIATED BY G PROTEINS

| Stimulus | Receptor | G protein[a] | Effector | Physiological Response | Reference |
|---|---|---|---|---|---|
| f-Met peptide | Chemotactic receptor | $G_{PLC}$ | Phospholipase C | Chemotaxis | Krause et al. 1985 |
| Acetylcholine | Muscarinic receptor | $G_K$ | Potassium channel | Slowing of pacemaker activity | Pfaffinger et al. 1985<br>Breitwieser & Szabo 1985 |

[a] $G_{PLC}$ and $G_K$ refer to as yet unidentified G proteins in these cascades.

Many cell surface receptors (e.g. tyrosine-specific protein kinases) are "single-pass" transmembrane proteins having a catalytic domain exposed on the cytoplasmic side of the plasma membrane. Their structure is simple: a single extracellular ligand-binding domain joined to a single intracellular domain which effects a change in the cytoplasm when the receptor binds ligand. In receptors of this class located on cell surfaces, the two domains are connected by means of a single highly hydrophobic region, generally of 20 to 25 residues and displaying o helical structure, which embeds the receptor in the cell membrane. For such membranes a conformational change propagates across the lipid bilayer through the single transmembrane alpha helix.

G-protein-linked receptors have a more complex structure. They share structural features including a bundle of seven hydrophobic, largely α-helical membrane-spanning segments ("spans") of 20 to 28 amino acids each, joined by hydrophilic loops. (J. Findlay and D. Pappin, *Biochem J.* 238:625 (1986); C. Strader et al. (1989) *FASEB J.* 3:1825 (1989), both incorporated herein by reference). Ligands are proposed to bind within the bundle of helices, perhaps deeply, such that an agonist can alter inter-helix packing to induce a conformational change on the receptor's cytoplasmic face. Thus the site for ligand binding is formed from the interaction of a number of spans with each other and possibly with extracellular and/or intracellular regions of the receptor as well. One study concluded that ligand binding specificity is determined by most of the transmembrane regions of the receptor (T. Friele et al., *Proc. Natl. Acad. Sci. USA* 85:9494 (1988). Other structural characteristics shared by these receptors include consensus sites for N-linked glycosylation near the amino terminus, three short extracellular loops, two short, cationic cytoplasmic loops, and a longer third cytoplasmic loop (called the "i3 loop") that connects spans five and six. Sequence homology among the receptors is highest in the membrane-spanning regions, and exists to a lesser extent in the shorter connecting loops. The cytoplasmic carboxy-terminal region and the i3 loop display minimal sequence homology even among closely related receptors, and their lengths can vary dramatically.

B. Functional features

1. Ligand binding

Several generalizations have been suggested regarding structure-function relationships within the G-protein-linked receptor molecule (reviewed in C. Strader et al., *FASEB J.* 3:1825 (1989); E. Parker and E. Ross, In *Current Topics in Membranes & Transport*, T. Claudio, ed. New York: Academic Press (1989); and H. Dohlmann et al., *Biochemistry* 26:2657 (1987), all of which are incorporated herein by reference).

The agent bound by or reacting with a receptor is called a "ligand", a term which is definitionally meaningful only in terms of its counterpart receptor. The term "ligand" does not imply any particular molecular size or other structural or compositional feature other than that the substance in question is capable of binding or otherwise interacting with the receptor. A ligand capable of reacting with a receptor and initiating an effect is said to possess both affinity and efficacy and is termed an agonist; a compound which is itself devoid of intrinsic pharmacological activity but causes effects by inhibiting the activity of a specific agonist (e.g., by competition for agonist binding sites) is termed an antagonist. The effects of two ligands on the same receptor may be additive or one ligand may antagonize another, depending upon their relative concentrations and efficacies. See, L. Goodman and A. Gilman, p.35 in *The Pharmacological Basis of Therapeutics*, 7th ed. Macmillan (1985), incorporated herein by reference. It is understood in the present invention that one may employ the method herein described to screen for agents acting as agonists alone or as agonists or antagonists in relation to another ligand.

Many receptor types bind ligands by their extracellular domains. Ligand binding by the structurally complicated G-protein-linked receptors is likewise more complicated. Ligands are thought to bind to their respective G-protein-linked receptors within the hydrophobic core in a pocket formed by the bundle of membrane-spanning helices. Evidence for this hypothesis was provided by photoaffinity labelling experiments (S. Wong et al,, *J. Biol. Chem.* 263:7925 (1988); C. Curtis et al., *J. Biol. Chem.* 264:489 (1989); both incorporated herein by reference), the introduction of point mutations into the receptor protein (summarized by C. Strader et al., *FASEB J.* 3:1825 (1989), incorporated herein by reference), and chimeric receptor studies (B. Kobilka et al. (*Science* 240:1310 (1988), all of which are incorporated herein by reference. Most of the amino- and carboxy-terminal regions and most of the i3 loop are probably not required for ligand binding (R. Rubenstein et al., *J. Biol. Chem.* 262: 16655 (1987); C. Strader et al., *J. Biol. Chem.* 262:16439 (1987), both of which are incorporated herein by reference).

2. G-protein regulatory domains

The domain of the receptor most likely to bind and regulate G proteins is expected to be found on the cationic cytoplasmic region of the receptor, since the GTP binding α subunits of the G proteins are located at the cytoplasmic surface of the plasma membrane.

Indeed, several studies have implicated the i3 loop as being important in specifying G-protein interactions (T. Frielle et al., *Proc. Natl. Acad. Sci. USA* 85:9494 (1988); B. Kobilka et al., Science 240:1310 (1988); T. Kubo et al., *FEBS Lett.* 241:119 (1988); J. Wess et al. *FEBS Lett.* 258:133 (1989); S. Wong et al. *J. Biol. Chem.* 265:6219 (1990); S. Cotecchia et al. *Proc. Natl. Acad. Sci. (USA)* 87:2896 (1990); all of which are incorporated herein by reference).

It is the regions closest to the amino- or carboxy-terminal ends of the i3 loop which are evidently involved in binding and regulating G proteins. G protein regulation is sensitive to relatively slight mutations in these regions (R. Franke et al., *J. Biol. Chem.* 263:2119 (1988); B. O'Dowd et al., *J. Biol. Chem.* 263:15985 (1988); all of which are incorporated herein by reference). Deletion of several small segments from the middle portion of the i3 loop of the hamster β2-adrenergic receptor does not affect G protein coupling (R. Dixon et al., *Nature* 326:73 (1987); C. Strader et al., *J. Biol. Chem.* 262 16439 (1987); all of which are incorporated herein by reference) However, deletion of sequences at the amino- and carboxy-terminal portions of the i3 loop in this receptor leads to loss of G-protein activation, including a region of eight amino acids forming the junction between the carboxy-terminus of the fifth transmembrane helix and the i3 loop (C. Strader et al., *J. Biol. Chem.* 262:16439 (1987), incorporated herein by reference).

A segment as short as 12 amino acids at the amino-terminal end of the i3 loop is a major determinant of how efficiently individual muscarinic receptors are coupled to G-proteins (Wong et al., 1990, incorporated herein by reference). Other regions of i3 loop may not be required for G-protein coupling. The large central section of the i3 domain of the β-adrenergic receptor is not required for coupling, for instance (Rubenstein, et al. (1987) *J. Biol. Chem.* 262:16655; Strader et al. (1987) *J. Biol. Chem.* 262:16439; both incorporated herein by reference).

3. Effectors

As mentioned previously, G proteins regulate a number of intracellular effectors including, among others, adenylyl cyclase, the retinal cGMP phosphodiesterase, phospholipase A2 and C activities, and a wide variety of ion channels. Membrane transport proteins are also regulated by G-proteins, including those for Mg2+ uptake and glucose transport.

Each G protein is a heterotrimer of a GTP binding α subunit and regulatory β and γ subunits. The α subunit defines the specific interactions of a G protein with its effector. Each is assumed to have a distinct receptor binding domain sufficiently distinct to be selective for appropriate receptors.

There are more than 25 different cell-surface receptors that have been shown to utilize the inositol-phospholipid transduction pathway, in which ligand binding leads to increased $[Ca^{+2}]_i$. Many others (e.g., human D1 dopamine receptor) operate via different signal transduction pathways. (For mechanisms of signal transduction by G-protein-linked receptors see, pp. 735ff B. Alberts et al., *Molecular Biology of the Cell*, Garland Publishing: London (1983), incorporated herein by reference).

II. Polypeptides

This invention employs chimeric receptor proteins in a method of screening for agents reacting with G-protein linked receptors.

The term "G-protein-linked receptor" refers to any protein either derived from a naturally occurring G-protein-linked receptor, or which shares significant structural and functional characteristics peculiar to a naturally occurring G-protein-linked receptor, as described previously. Such a receptor may result when regions of a naturally occurring receptor, such as membrane-spanning domains, the amino- or carboxy-terminal tails, or hydrophilic loops are deleted or replaced in such a manner as to yield a protein having a similar function. Homologous sequences, allelic variations, and natural mutants; induced point, deletion, and insertion mutants; alternatively expressed variants; proteins encoded by DNA which hybridize under high or low stringency conditions to nucleic acids which encode naturally occurring G-protin-linked receptors; proteins retrieved from naturally occurring materials; and closely related proteins retrieved by antisera directed against G-protein-linked receptor proteins are also included.

Mutants of the receptor may include genetic variants, both natural and induced. Induced mutants may be derived from encoding nucleic acids using irradiation or exposure to chemical mutagens such as EMS, or may take the form of engineered changes by site-specific mutagenesis or other techniques of modern molecular biology. See, e.g., Sambrook, Fritsch and Maniatis (1989), *Molecular Cloning: A Laboratory Manual* (2nd ed ), CSH Press, incorporated herein by reference.

G-protein-linked receptors belong to different classes, categorized on the basis of the effects, or lack of effects, of representative agonists and antagonists, and by the relative potencies of representative agonists. The receptors for epinephrine and norepinephrine, for example, are designated as alpha- or beta-adrenergic receptors on the basis of the effects of several representative sympathomimetic amines and adrenergic blocking agents. See, L. Goodman and A. Gilman, pp. 39–40 in *The Pharmacological Basis of Therapeutics*, 7th ed. Macmillan, (1985), incorporated herein by reference. It is understood in the present invention that a G-protein-linked receptor "of a different class" would include a receptor distinguished on the basis of the effects of a ligand upon the receptor as well as one distinguished on the basis of receptor binding of different ligands, such as the distinction between acetylcholine and adrenergic receptors. The various muscarinic acetylcholine receptors (e.g., m1, m2, etc.), on the other hand, are examples of subtypes of receptors existing within the same receptor class.

The term "G-protein-coupling polypeptide" refers to any polypeptide which provides G-protein-coupling specificity to a G-protein-linked receptor. In the chimeric receptors of this invention, the G-protein-coupling specificity provided to the chimeric receptor will allow it to cause an increase in $[Ca^{+2}]_i$ as a result of agonist binding, a function not provided by the parental G-protein-linked receptor whose sequences the G-protein-coupling polypeptide replaces or into which this polypeptide is inserted.

The term "chimeric G-protein-linked receptor" refers to any G-protein-linked receptor protein which contains a G-protein-coupling polypeptide replacing or in addition to analogous sequences on that parental G-protein-linked receptor. This foreign G-protein-coupling polypeptide would give the chimeric receptor the ability to interact with and activate (or inhibit) a different G protein than would normally be the case, and thus effect a different biochemical effect in the cell in response to ligand binding by the chimeric receptor.

In one embodiment of the invention, such a chimeric receptor will be generated by the insertion of a foreign G-protein-coupling polypeptide into a G-protein-linked receptor, preferably into the i3 loop of a G-protein-linked receptor. Such insertions can easily be accomplished by recombinant DNA technology, for instance, by inserting a nucleic acid sequence encoding a G-protein-coupling polypeptide into a suitable restriction site of a nucleic acid sequence encoding a G-protein-linked receptor in such a fashion that the two sequences are in the correct reading frame.

A preferable embodiment of the invention involves the replacement of portions of a parental G-protein-linked receptor by a foreign G-protein-coupling polypeptide. Such a replacement is likewise easily accomplished by recombinant DNA techniques, as described below, and especially by the use of the polymerase chain reaction (PCR) technique. Such a chimeric receptor will preferably be made by the limited replacement of the amino- and/or carboxy-terminal ends of the i3 loop; more preferably yet by replacement of the entire i3 loop and additional adjacent regions with a foreign G-protein-coupling polypeptide; and most preferably by replacement of an i3 loop of a parental G-protein-linked receptor with a foreign G-protein-coupling polypeptide. The G-protein-coupling polypeptide used in these replacements will usually provide sequences analogous to those it replaces; for instance, where an entire i3 loop is replaced, the foreign G-protein-coupling polypeptide will usually comprise a polypeptide substantially homologous to an entire i3 loop; where a region of 16 amino acids is replaced, the foreign G-protein-coupling polypeptide will usually comprise a polypeptide of approximately 16 amino acids; and so on. These examples of insertion and replacement are simply meant to be illustrative and not to limit the types of insertions and replacements claimed herein.

The term "substantial homology", when referring to polypeptides, indicates that the polypeptide or protein in question exhibits at least about 30% homology with an entire naturally occurring protein or a portion thereof, usually at least about 70% homology, and preferably at least about 95% homology. For comparisons between G-protein-linked receptors, especially from different receptor families, this homology will be expected to be highest in the hydrophobic membrane-spanning regions, while overall homology may be far lower, and a less important indicator. Between hamster β-adrenergic receptor and turkey β-adrenergic receptor, overall amino acid homology is 49%, yet the intramembranous regions are 73% homologous and the first two cytoplasmic loops are 64% homologous, while the amino- and carboxy-terminal regions are only 18% and 20% homologous, respectively. Similar results are seen for other G-protein-linked receptors (H. Dohlman, et al., *Biochemistry* 26:2657 (1987), incorporated herein by reference.

It is important to distinguish the chimeric receptors of this invention from others described by Dull et al. (U.S. Pat. No. 4,859,609). Dull et al. describe and claim "single-pass" receptors with a single transmembrane region (which may not be present at all in secreted receptor proteins). The amino terminus of the receptor extends into the extracellular space where it binds ligand; the carboxy terminus extends into the cytoplasm where it effects a biochemical response to ligand binding by the extracellular domain. Indeed the structure of such a chimeric receptor is described as comprising "the ligand binding domain of a receptor fused at its C-terminus to the N-terminus of a heterologous reporter polypeptide." (page 2, lines 62-64). In each case where membrane spanning regions are referred to, the language reads "a transmembrane region"—only a single pass through the membrane is described and claimed. See also, FIG. 4 in Dull et al. Indeed, such a description embraces a large number of important cellular receptors. It is inadequate, however, to describe G-protein-linked receptors as described herein. The conserved structure characteristic of these receptors, as mentioned previously, contains seven membrane spanning regions. Ligand binding and the signal transduction resulting therefrom involve the interaction of a number of residues on at least three different spanning regions which can interact properly with the ligand only as a result of the maintenance of correct inter-helix packing (C. Strader et al., *FASEB J.* 3:1825 (1989); E. Ross, *Neuron* 3:141 (1989); both incorporated herein by reference). Such complex structures, necessary to the proper G-protein-linked receptor function are not comprehended by the single-pass chimeric receptors of Dull et al.

The G-protein-coupling polypeptide used in this invention will usually comprise at least about 5 amino acids, more usually at least about 10 amino acids, more usually at least about 12 to 16 amino acids, and preferably the entire i3 loop. It will have substantial homology to all or part of the i3 loop of a naturally occurring G-protein-linked receptor, especially the amino-terminal end of the i3 loop. It may also include the entire i3 loop or the i3 and adjacent loops.

As used herein, the terms substantially pure and substantially homogenous describe a protein which has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially pure protein will typically comprise over about 85 to 90% of a protein sample, more usually about 95%, and preferably will be over about 99% pure. Normally, purity is measured on a polyacrylamide gel, with homogeneity determined by visualizing a single polypeptide band upon staining. For certain purposes high resolution will be needed and HPLC or a similar means for purification utilized. For most purposes, a simple chromatography column or polyacrylamide gel will be used to determine purity.

A polypeptide is substantially free of naturally-associated components when it is separated from the native contaminants which accompany it in its natural state. Thus, a polypeptide which is chemically synthesized or synthesized in a cellular system different from the cell from which it naturally originates (or in the present invention, the cell from which the parental first G-protein-linked receptor, which is altered by substitution or replacement, originates) will be substantially free from its naturally-associated components. The term is used to describe receptors and nucleic acids which have been synthesized in heterologous mammalian, insect, or plant cells, or *E. coli* and other prokaryotes, for example.

III. Nucleic acids

Chimeric receptors will typically be made by synthetic polypeptide methods or more preferably by recombinant nucleic acid methods. Recombinant methods for synthesis of the chimeric receptor commence with the construction of a replicable vector containing nucleic acid that encodes the hybrid receptor. Vectors typically facilitate the cloning of the nucleic acid encoding the hybrid receptor, i.e., to produce usable quantities of the nucleic acid. They also direct the expression of the hybrid receptor. One or both of these functions are performed by the vector-host system. The vectors will contain different components depending upon the function they are to perform as well as the host cell that is selected.

Techniques for nucleic acid manipulation are described generally, for example in Sambrook et al., *Molecular Cloning: A Laboratory Manual* (2nd ed.), Vols. 1-3, Cold Spring Harbor Laboratory, (1989) which are incorporated herein by reference. Techniques for synthesis of polypeptides are described, for example, in Merrifield, *J. Amer. Chem. Soc.* 85:2149-2156 (1963), incorporated herein by reference. The recombinant nucleic acid sequences used to produce fusion proteins of the present invention may be derived from natural or synthetic sequences. Many natural gene sequences are obtainable from various cDNA or from genomic libraries using appropriate probes. See, Genbank(TM), National Institutes of Health, incorporated herein by reference. Techniques for making and screening cDNA and genomic libraries to obtain gene sequences of interest are described, e.g., in *Current Protocols in Molecular Biology*, F. Ausubel et al., ed. Greene Publishing and Wiley-Interscience, New York (1987), incorporated herein by reference. It may be advantageous to employ the polymerase chain reaction (PCR) to synthesize gene sequences from genomic DNA or messenger RNA (mRNA), as necessary, using primers derived from published DNA sequences or degenerate primers derived from protein sequence. PCR may also provide important advantages in the construction of chimeric proteins, as described below. See, e.g., *PCR Protocols: A Guide to Methods and Applications.* (Innis, M, Gelfand, D., Sninsky, J and White, T., eds.), Academic Press, San Diego (1990), incorporated herein by reference. Typical probes and primers for G-protein-linked receptors may be selected from published sequences in accordance with published procedures. A double stranded fragment may then be obtained by annealing the strands together under appropriate conditions or by adding the complementary strand using DNA polymerase with an appropriate primer sequence.

The nucleic acid sequences will usually comprise at least about 10 nucleotides, more usually at least about 30 nucleotides, and preferably at least about 50 nucleotides. One or more introns may also be present. The length of nucleic acid sequences employed will depend on the use: hexamers are useful in making labelled nucleotide probes; oligonucleotides as short as 15-mers or shorter are useful in hybridizations; sequences encoding G-protein-linked receptors may be many hundreds of nucleotides in length.

"Substantial homology" (or "substantial similarity"), when referring to nucleic acids, means either that the segments, or their complementary strands, when optimally aligned and compared, are identical with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to a strand, or its complement, typically using a sequence derived from naturally occurring sequences published in the literature. Selectivity of hybridization exists when hybridization occurs which is more selective than total lack of specificity. Typically, selective hybridization will occur when there is at least about 55% homology, preferably at least about 65%, more preferably at least about 75%, and most preferably at least about 90%. See, M. Kanehisa *Nucleic Acids Res.* 12:203 (1984), incorporated herein by reference. Stringent hybridization conditions will typically include salt concentrations of less than about 1M, more usually less than about 500 mM and preferably less than about 200 mM. Temperature conditions will typically be greater than 22° C., more typically greater than about 30° C. and preferably in excess of about 37° C. As other factors may dramatically affect the stringency of hybridization, including base composition and size of the complementary strands, presence of organic solvents and extent of base mismatching, the combination of parameters is more important than the absolute measure of any one alone.

The nucleic acids claimed may be present in whole cells, in a cell lysate, or in a partially purified or substantially pure form. A nucleic acid is rendered substantially pure when purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

The nucleic acid compositions of this invention may be derived from genomic DNA or cDNA, prepared by synthesis or may be a hybrid of the various combinations. Recombinant nucleic acids comprising sequences otherwise not naturally occurring are also provided by this invention.

Synthetic oligonucleotides can be formulated by the triester method according to Matteucci, et al., *J. Am. Chem. Soc.*, 103:3185 (1981) or by the phosphoramidite method described by Beaucage and Carruthers, *Tetra. Letts.* 22:1859-1862 (1981), both of which are incorporated herein by reference, or by other methods such as commercial automated oligonucleotide synthesizers.

Nucleic acid probes used for constructing nucleic acids encoding chimeric receptor proteins, for obtaining sequences encoding naturally occurring G-protein-linked receptors from cDNA or genomic libraries, or other purposes will include an isolated nucleic acid attached to a label or reporter molecule. Probes may be prepared by nick translation, Klenow fill-in reaction, random hexamer priming, or other methods known in the art. For making probes, see, e.g., *Current Protocols in Molecular Biology*, F. Ausubel et al., ed. Greene publishing and Wiley-Interscience, New York (1987), incorporated herein by reference.

The natural or synthetic nucleic acids encoding a desired chimeric G-protein-linked receptor will typically be incorporated into expression vectors. Commonly DNA expression vectors incorporating coding regions for the receptor will be suitable for replication in a unicellular host, such as yeast or bacteria, but may also be intended for introduction to, and possibly introduction into the genome of, a cultured mammalian or plant or other eukaryotic cell lines. DNA constructs prepared for introduction into bacteria or yeast will typically include a replication system recognized by the host, the intended DNA fragment encoding the desired receptor protein, and transcription and translational initiation regulatory sequences operably linked to the polypeptide encoding segment. The transcriptional regulatory sequences will typically include a heterologous enhancer and/or promoter which is recognized by the host.

The selection of an appropriate promoter will depend upon the host, but bacterial promoters such as the trp, lac and phage promoters, tRNA promoters and glycolytic enzyme promoters are known and commonly used. See, Sambrook et al. (1989), incorporated herein by reference. Useful yeast promoters include the promoter regions for metallothionein; 3-phosphoglycerate kinase or other glycolytic enzymes such as enolase, glyceraldehyde-3-phosphate dehydrogenase; enzymes responsible for maltose and galactose utilization; and others. Suitable vectors and promoters for use in yeast expression are further described in R. Hitzeman et al., EP 73,657A, incorporated herein by reference. Appropriate non-native mammalian promoters might include the early and late promoters of SV40 or promoters derived from mouse mammary tumor virus, avian sarcoma viruses, adenovirus II, bovine papilloma virus or polyoma virus, among others. For other expression systems conveniently available expression vectors which include the replication system and transcriptional regulatory sequences together with the insertion site for the receptor protein coding sequence may be employed. Examples of workable combinations of cell lines and expression vectors are described in Sambrook et al. (1989); see also, Metzger et al. *Nature* 334:31 (1989), incorporated herein by reference.

Propagation of mammalian cells in culture is per se well known. See, *Tissue Culture*, Academic Press, Kruse and Patterson, ed. (1973), incorporated herein by reference. Examples of useful mammalian host cell lines are VERO and HeLa cells, Chinese hamster ovary (CHO) cells, and WI38, BHK, and COS cell lines. Other hosts may include such organisms as bacteria (e.g., *E. coli* or *B. subtilis*), yeast or filamentous fungi, plant cells, insect cells, and amphibian or avian cells, including Xenopus oocytes, among others.

Expression vectors for these cells can include expression control sequences, such as an origin of replication or autonomously replicating sequence (ARS), a promoter, an enhancer and necessary processing information sites, such as ribosome-binding sites, RNA splice sites, polyadenylation sites, transcriptional terminator sequences and mRNA stabilizing sequences. The enhancers or promoters may, where appropriate, be those naturally associated with genes encoding G-protein-linked receptors, although it will be understood that in many cases others will be equally or more appropriate. Other preferred expression control sequences are enhancers or promoters derived from viruses, such as SV40, adenovirus, bovine papilloma virus, and the like. See, *Enhancers and Eukaryotic Gene Expression*, Cold Spring Harbor Press, N.Y. (1983), incorporated herein by reference.

Such expression vectors will also include secretion signals, whether from a native G-protein-linked receptor or from other receptors or from secreted polypeptides of the same or related species, which allow the protein to cross and lodge in cell membranes, and thus attain its functional topology.

While such expression vectors may replicate autonomously, they may less preferably replicate by being inserted into the genome of the host cell, by methods well known in the art.

Expression and cloning vectors will likely contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker will depend on the host cell, and appropriate markers for different hosts are well known in the art.

The vectors containing the nucleic acids of interest can be transcribed in vitro and the resulting RNA introduced into the host cell by well-known methods (e.g., by injection. See, T. Kubo et al., *FEBS Lett.* 241:119 (1988), incorporated herein by reference, or the vectors can be introduced directly into host cells by well known methods, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., (1989) and F. Ausubel et al. (ed.), (1987), both incorporated herein by reference. The cells into which have been introduced nucleic acids described above are meant to also include the progeny of such cells.

Such expression systems can produce chimeric receptor proteins in high quantities. The proteins may, where required, be purified to substantial homogeneity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

A nucleic acid is operably linked when it is placed into a functional relationship with another nucleic acid sequence. For instance, a promoter or enhancer is operably linked to a coding sequence if it affects the transcription of the sequence. Generally, operably linked means that the DNA sequences being linked are contiguous and, where necessary to join two protein coding regions, contiguous and in reading frame.

IV. Methods for use

The method of screening for agents reacting with the chimeric G-protein-linked receptors described herein provides a powerful tool for basic research into receptor function as well as for drug discovery efforts.

Typically, radioisotopic ligand binding and second messenger assays are employed in screening ligands for their interaction with G-protein-linked receptors. In the former assay, radioisotopic labeled ligands are incubated with cells expressing the receptors on their cell surface. One then measures the displacement of the label from the receptors by various concentrations of unlabeled agents. See, for example, binding assays in J. Wess et al., *FEBS Lett.* 258:133 (1989); B. O'Dowd et al., *J. Biol. Chem.* 263:15985 (1988); S. Cotecchia et al., *J. Biol. Chem.* 265:63 (1990); all incorporated herein by reference.

One may also measure such activities as phosphoinositide breakdown (J. Wess et al., *FEBS Lett.* 258:133 (1989), incorporated herein by reference), the generation of electrical currents resulting from ion movements across cell membranes (e.g., T. Kubo et al., *Nature* 323:411 (1986), incorporated herein by reference), or the formation of second messengers, e.g., by adenylyl cyclase activity (e.g., E. Ross, *J. Biol. Chem.* 257:10751 (1982), incorporated herein by reference).

These assay methods are difficult, expensive and time consuming to perform and commonly involve the use of hazardous reagents.

Another assay, that for $[Ca^{+2}]_i$, has many advantages, but is applicable only to those naturally occurring G-protein-linked receptors which utilize the inositol-phospholipid signal transduction pathway. Many others operate via different pathways.

Using cells expressing the chimeric G-protein-linked receptors described above, it is possible to make such receptors capable of elevating $[Ca^{+2}]_i$ if they do not do so in their native form.

The preferred assay for elevated $[Ca^{+2}]_i$ involves the use of a fluorescent dye. The cells are incubated in a solution containing the fluorescent dye, then washed and their fluorescence measured by means of a spectrofluorimeter. The test ligand is added to the cells, now loaded with the dye. Alternatively, the cells may be preincubated with an antagonist or agonist of the ligand before binding of the test ligand. Finally, the fluorescence of the cells is again measured, and the two fluorescence values compared.

This test is inexpensive, safe and facile, and the $[Ca^{+2}]_i$ response is rapid and robust. With appropriate automation of the calcium assay, it may be possible to screen large numbers of compounds as agonists or antagonists of any previously cloned member of the G-protein-linked receptor family and avoid the hazards and costs associated with the use of radioisotopes.

Cells expressing these chimeric receptors will have had nucleic acids encoding these receptors introduced into them by methods described above. These cells are commonly mammalian cells.

Various fluorescent dyes may be employed in the assays for $[Ca^{+2}]_i$. Examples include, but are not limited to, Fura-2, Quin-2, Indo-1, and Fluo-3 (see, R. Tsien, *Methods in Cell Biol.* 30:127–156, incorporated herein by reference).

The invention will better be understood by reference to the following example, which is intended to merely illustrate the best mode now known for practicing the invention, but the invention is not to be considered limited thereto.

EXAMPLE

Cloning of protein coding region of human m1 muscarinic acetylcholine and D2 domamine receptor genes and construction of a D2/m1 receptor chimera The protein coding portion of the human m1 muscarinic acetylcholine receptor gene was cloned from human genomic DNA by PCR (S. Scharf, pp. 177–183 in *PCR Protocols: A Guide to Methods and Applications.* Innis, M., et al., eds. Academic Press, San Diego (1990), incorporated herein by reference) using primers derived from the published DNA sequences (W. Allard et al, *Nucleic Acids Res.* 15:10604 (1987); E. Peralta et al., *EMBO J.* 6:3923 (1987), both of which are incorporated herein by reference) (5'-CGGAATTCCCAGCC-CCACCT AGCCACCA-3' (SEQ. ID No. 1) and 5'-GGGGATCCGA GGGATGCAGGAGAGG-GGAC-3') (SEQ. No. 2). Amplification was carried out in a 30 cycle, 25 µl reaction containing 0.5 µg of human placental DNA (Sigma) using the GeneAmp TM kit (Perkin-Elmer Cetus) according to the manufacturer's recommendations. The amplified m1 receptor DNA was cloned into the mammalian expression vector pBJ1-Neo (A. Lin et al., *Science* 249:677 (1990), incorporated herein by reference) to produce the m1 receptor expression plasmid pSRm1-9. The m1 receptor insert of pSRm1-9 was sequenced (F. Tonnequzzo et al., *Biotechnicues* 6:460 (1988), incorporated herein by reference) and found to code for the same peptide sequence as one of the published clones (W. Allard et al., *Nucleic Acids Res.* 15:10604 (1987), incorporated herein by reference).

The coding portion of the cDNA for the short form of the human $D_2$ dopamine receptor ($D_{2(414)}$) was cloned from a λgt10 human retina cDNA library by PCR, using primers derived from the published sequences (D. Grandy et al., *Proc. Natl. Acad. Sci. USA* 86:9762 (1989); R. Dal Toso et al., *EMBO J.* 8:4025 (1989); T. Storman et al., *Mol. Pharmacol.* 37:1 (1990), all of which are incorporated herein by reference) (5'-GCGAATT-CATGGATCCACTG AATCTGTCC-3' (SEQ. ID No. 3) and 5'-GATAAGCTTC AGCAGTGGAG-GATCTTCAG-3') (SEQ. ID No. 4). Two µg of phage DNA was used as template in a 30 cycle, 100 µl PCR reaction and the amplified $D_{2(414)}$ receptor fragment was cloned into pBJ1-Neo. The DNA sequences of the inserts of two recombinant plasmids were determined and each was found to contain a different point mutation introduced by the PCR amplification. Therefore, non-mutant restriction fragments from each clone were ligated together and re-cloned into pBJ1-Neo to produce the $D_{2(414)}$ receptor expression plasmid pSRD2(414)-C.

The $D_2$/m1 receptor chimera was made by the recombinant PCR technique (R. Higuchi, pp. 177–183 in *PCR Protocols: A Guide to Methods and Applications,* M. Innis et al., eds. Academic Press, San Diego (1990), both of which are incorporated herein by reference). Primers with sequences 5'-CTTCATTGTC ACCCTGCTGG TCTACTGGCGCATCTACCGG GAGA-3' (SEQ. ID No. 5) and 5'-GAACACGCCG AGAACAATGG CGAGGGTCCGAGCCGCCTTC TTCTC-3' (SEQ. ID No. 6) were used in a 10 cycle, 100 µl PCR reaction containing 400 ng of linearized pSRM1-9 to amplify a fragment coding for the third cytoplasmic loop of the m1 receptor fused at each end to sequences coding for the homologous portions of the fifth and sixth transmembrane segments of the $D_2$ receptor. 35 ng of this chimeric DNA fragment was then used to prime a 10 cycle, 100 µl PCR reaction containing 2 µg of the λ phage library DNA described previously. Next, the $D_2$ receptor primers described previously were added to the reaction and 30 additional PCR cycles were performed and the PCR reaction products were cloned into pBJ1-Neo. As with the $D_{2(414)}$ receptor clone, the sequences of two $D_2$/m1 chimeric clones were analyzed and found to contain non-identical, PCR-induced errors, so restriction fragments from each clone were combined to make the $D_2$/m1 expression clone pSRD2m1-C.

This expression clone was deposited on Jun. 16, 1993 in the American Type Culture Collection, 12301 Parklawn Drive, Rockville, Md. 20852 as ATCC 75487 pursuant to the provisions of the Budapest Treaty.

FIG. 1 shows a schematic of the $D_2$/m1 receptor that was constructed. In contrast to previously published G-protein-linked receptor chimeras (B. Kobilka et al., *Science* 240:1310 (1988); 1. Kubo et al., *FEBS Lett.*

24:119 (1988); J. Wess et al. *FEBS Lett.* 258:133 (1989); S. Wong et al. *J. Biol. Chem.* 265:6219 (1990); S. Cotecchia et al. *Proc. Natl. Acad. Sci. (USA)* 87:2896 (1990); T. Frielle et al., *Proc. Natl. Acad. Sci. USA* 85:9494 (1988)), the $D_2$/ml chimera was synthesized entirely by PCR. Since it does not require the use of restriction enzymes, the PCR approach is much more flexible in its ability to create DNA sequences with desired inserts. The entire i3 loop of the m1 receptor was inserted at exactly the putative ends of transmembrane helixes V and VI of the $D_{2(414)}$ receptor without introducing any amino acid changes. However, the PCR amplification produced sequence errors that had to be repaired by fusing the non-mutated portions of two $D_2$/ml clones. The use of thermostable polymerases with higher fidelity than Taq polymerase may enhance the ease with which chimeras with correct sequences can be constructed.

Mammalian cells expressing chimeric D2/ml receptor

CHO-K1 cells (American Type Culture Collection CCL 61) were grown in DMEM/F-12 1:1 (J. R. Scientific) containing 5% fetal bovine serum (HyClone), and 2 mM glutamine (J. R. Scientific). 40 μg of each receptor expression plasmid was linearized with Sca I and used to transfect $2 \times 10^6$ cells by electroporation (H. Potter, pp. 9.3.1-9.3.5 in *Current Protocols in Molecular Biology*, F. Ausubel et al., eds. Greene Publishing and Wiley-Interscience, N.Y. (1987), which is incorporated herein by reference). Cells were grown for 48 hrs. prior to the addition of 1 mg/ml G-418 sulfate (Geneticin; Gibco). The medium was replaced every three days and cells surviving the G-418 selection were grown and maintained in the selective medium. Experiments were done with cells harvested from 4 to 8 weeks after the initial transfection.

[$Ca^{+2}$]$_i$ Assay for ligand binding to chimeric D2/ml receptor

Cells were detached from culture flasks with EDTA, pelleted at $1,000 \times$ g and resuspended in $1 \times$ binding buffer (100 mM Tris; 120 mM NaCl; 5 mM KCl; 1 mM $MgCl_2$; 2 mM $CaCl_2$; 1.1 mM ascorbic acid; pH 7.4) at $\sim 1 \times 10^6$ cells/ml. Cells were homogenized with a Polytron (Brinkman) and the crude membrane fraction was pelleted at $17,000 \times$ g for 10 min. Membranes were resuspended in $1 \times$ binding buffer and $\sim 10$ μg of membrane protein from CHO-$D_{2(414)}$ cells or $\sim 20$ μg of protein from CHO-$D_2$/ml cells was used per 1 ml binding reaction. Triplicate binding reactions were done in IX binding buffer for 30 min. at 37°, then stopped by filtration through glass-fiber filters (Skatron) that were pre-soaked in 0.1% polyethyleneimine, followed by a 5 sec. wash with ice cold $0.1 \times$ binding buffer. Saturation binding experiments were done with 8 concentrations of [$^3$H]-spiperone (Amersham) in the range between 5 pM and 1 nM. Non-specific binding was defined with 10 μM fluphenazine. Competition binding experiments were performed with 500 pM [$^3$H]-spiperone and varying amounts of competing ligand. Competing ligands were all from Research Biochemicals Inc.

For [$Ca^{+2}$]$_i$ assays, cells from a single subconfluent 150 mm² T-flask were detached with EDTA, resuspended in Dulbecco's phosphate buffered saline (D-PBS) containing 0.1% glucose and 1 μM Fura2-AM (Molecular Probes Inc.), and incubated for 30 min. at 37°. The cells were then centrifuged at $750 \times$ g for 5 min. and resuspended in 40 ml of D-PBS containing 0.1% glucose. The cells were counted and then washed by centrifugation and resuspension in the same buffer at a concentration of $\sim 1 \times 10^6$ cells/ml. A 2 ml aliquot of the cell suspension was centrifuged and the cells were resuspended in fresh buffer immediately prior to use. Fluorescence was monitored with a DMX-1000 spectrofluorimeter (SLM-Aminco) equipped with a cuvette stirrer. The excitation wavelengths were 340 and 380 nm and the emission wavelength was 510 nm. The ratio of the intensities of the fluorescence at the two excitation wavelengths was used to calculate [$Ca^{+2}$]$_i$ as described previously (G. Grynkiewicz et al., *J. Biol. Chem.* 260:3440 (1988), incorporated herein by reference). For each experiment and each group of cells, maximum and minimum fluorescence values were determined by the addition of 10 mM digitonin followed by 10 mM EGTA.

Figure 2:
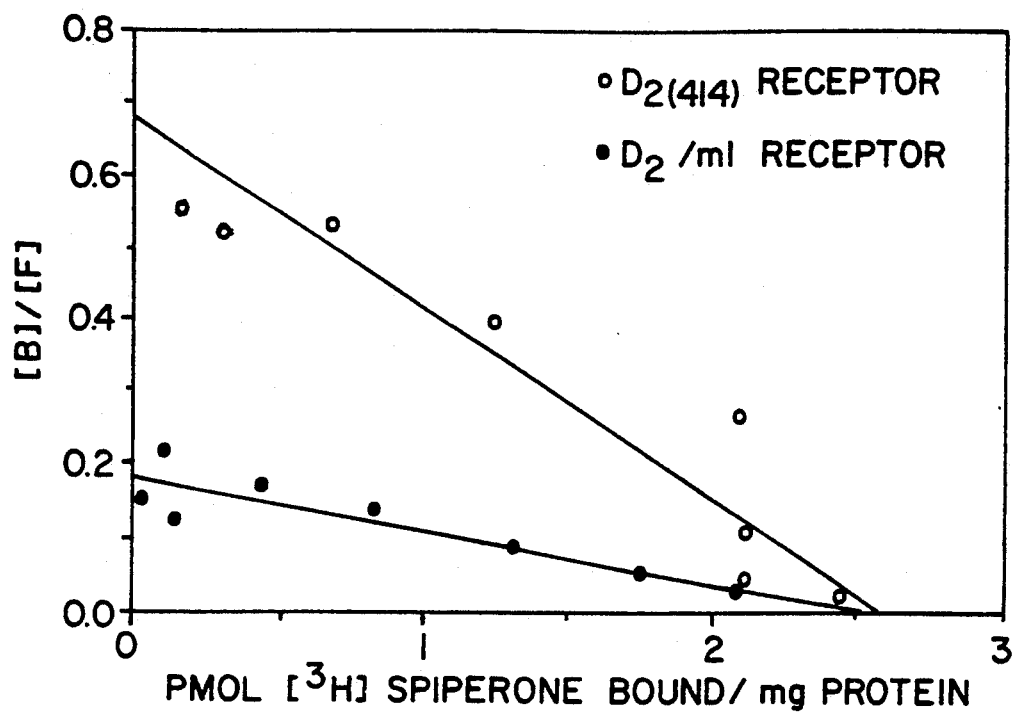
FIG. 2. Scatchard plot of [³H]-spiperone binding to D₂(414) and D₂/ml receptors. Specific binding of various hapten concentrations of [³H]-spiperone was determined in triplicate. The figure is a representative experiment.

Preliminary studies with CHO cells gave no detectable specific binding for the muscarinic ligand [$^3$H]-QNB or the dopaminergic ligand [$^3$H]-spiperone. Cells expressing ml, $D_{2(414)}$ or $D_2$/ml receptors were created by transfecting CHO-K1 cells with an expression vector containing the receptor DNA and a neo resistance gene. Transfected cells were then selected for G418 resistance. The pharmacological profiles of the $D_{2(414)}$ and $D_2$/ml receptors were compared to see what effect, if any, the substitution of the i3 loop from the m1 receptor had upon the chimeric receptor's affinity for dopaminergic ligands. Shown in FIG. 2 is a representative Scatchard plot of the binding of [$^3$H]-spiperone to crude membranes prepared from cells expressing either the $D_{2(414)}$ or the $D_2$/ml receptor. Mean $K_d$ and $B_{max}$ values from three experiments are calculated with the program LIGAND (P. Munson and D. Robard, *Anal. Biochem.* 107:220 (1980), incorporated herein by reference). The $K_d$ of $65 \pm 12$ pM (mean $\pm$ S.E.M. (n-3); $B_{max} = 4.0 \pm 1.1$ pmol/mg protein) determined for the $D_{2(414)}$ receptor agrees well with a previous determination of the $K_d$ for [$^3$H]-spiperone for the rat $D_{2(415)}$ receptor (J. Bunzow et al., *Nature* 336:783 (1988), which is incorporated herein by reference). The $D_2$/ml receptor shows a modest, but statistically significant ($p < 0.05$; t-test), decrease in [$^3$H]-spiperone affinity ($K_d = 250 \pm 10$ pM (n=3); $B_{max} = 3.8 \pm 0.6$ pmol/mg protein). Next, the binding affinities of six dopaminergic ligands were tested in a competition binding assay with [$^3$H]-spiperone. The results of three independent competition assays are summarized in Table 2. There was no difference in $K_i$'s of N-0434, (−)sulpiride and SKF-38393 for the $D_{2(414)}$ and $D_2$/ml receptor and although statistically significant ($p < 0.05$; t-test), the differences in the $K_i$ values for dopamine, fluphenazine and SCH-23390 were small.

TABLE 2

| $K_i$ VALUES (μM) FOR DOPAMINERGIC LIGANDS | | | | |
|---|---|---|---|---|
| | $D_{2(414)}$ Receptor | | $D_2$/ml Receptor | |
| Competitor | $K_i$ | 95% C.L. | $K_i$ | 95% C.L. |
| Fluphenazine | 0.0031 | (.0016, .0057) | 0.0072 | (.0053, .0098) |
| N-0434 | 0.021 | (.010, .042) | 0.027 | (.012, .058) |
| (−) Sulpiride | 0.028 | (.015, .054) | 0.045 | (.011, .180) |
| Dopamine | 6.0 | (4.9, 7.4) | 2.1 | (0.93, 4.63) |
| SCH-23390 | 2.1 | (1.5, 3.0) | 3.6 | (2.4, 5.3) |
| SKF-38393 | 21 | (8.8, 51) | 36 | (19, 70) |

Figure 3A:
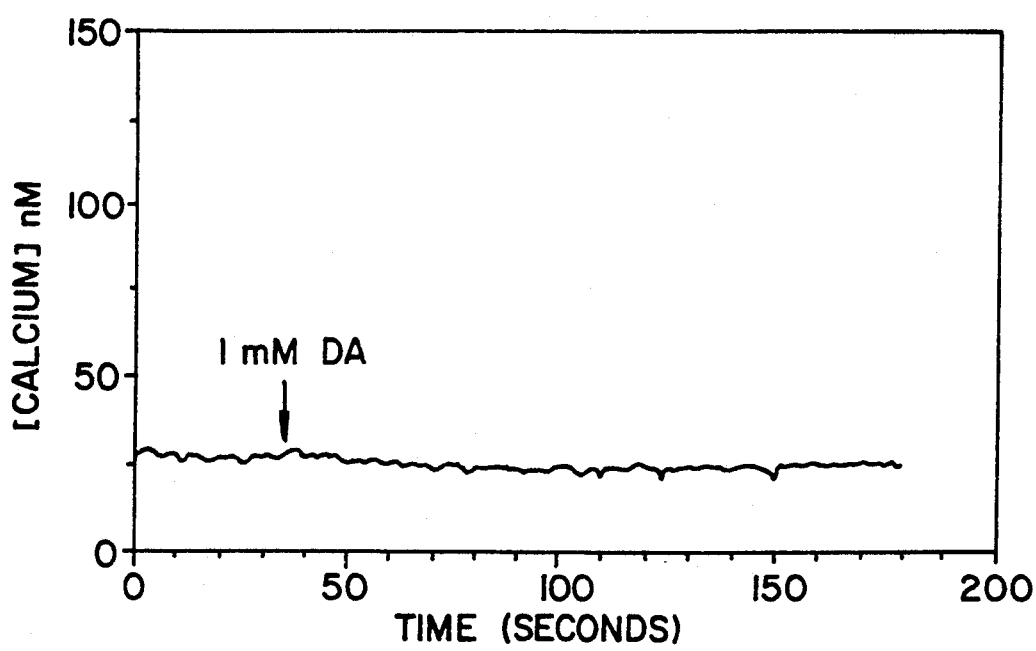
FIGS. 3A–3C. Effect of dopamine on $[Ca^{+2}]_i$ in Fura-2 loaded CHO cells.
Figure 3B:
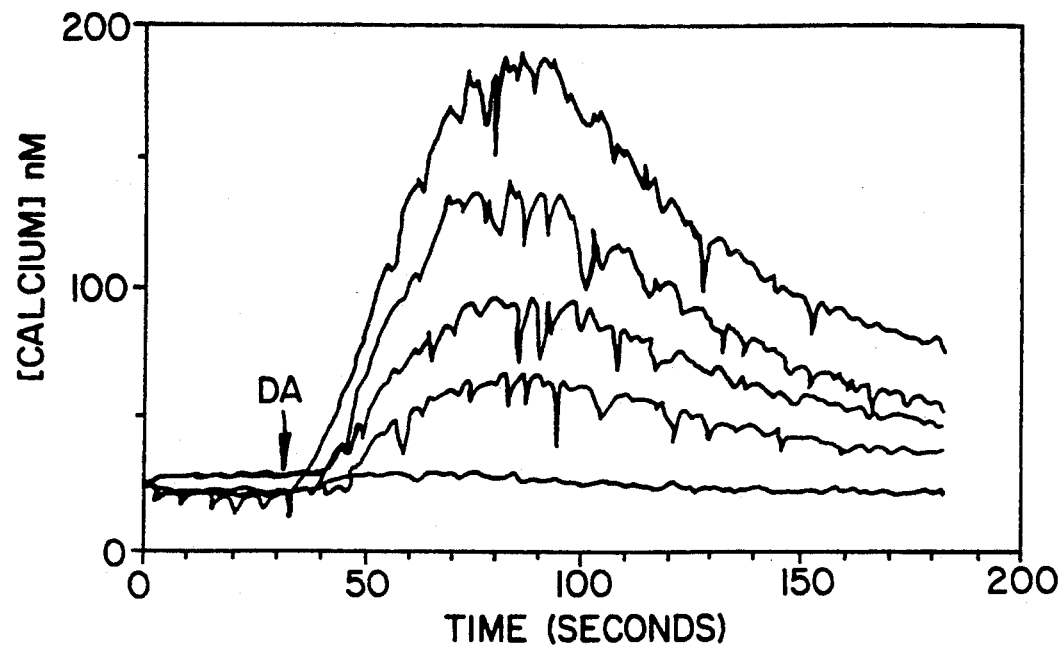
Figure 3C:
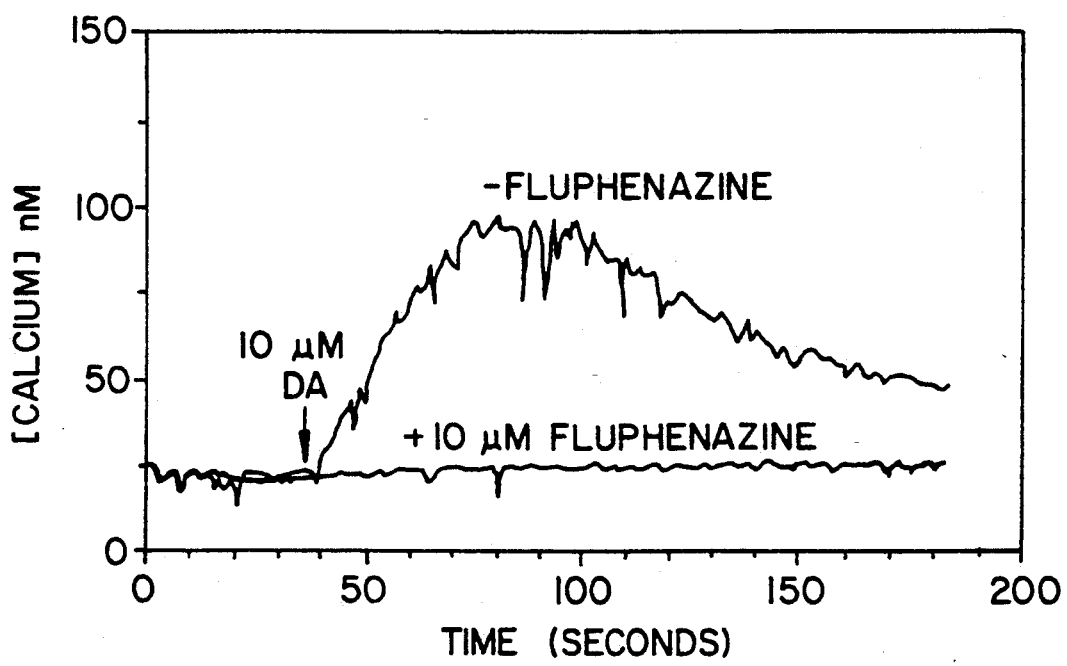

Preliminary studies with non-transfected CHO cells indicated that [$Ca^{+2}$]$_i$ was unaltered by carbachol (100 μM) or dopamine (1 mM). Activation of the human m1 receptor has been previously shown to lead to phosphatidylinositol hydrolysis and elevation of $[Ca^{+2}]_i$ (J. Lechleiter et al., in *Subtypes of Muscarinic Receptors IV*, Levine, R., and Birdsall, N., eds. *Trends Pharmacol. Sci. Suppl.*, pp. 34–38 (1989), which is incorporated herein by reference). When the human m1 receptor was expressed in CHO cells, it bound [$^3$H]-QNB with a $K_d$ of 81 pM and elevated $[Ca^{+2}]_i$ in a dose dependent manner in response to carbachol. The human $D_2$ receptor, on the other hand, is commonly thought to couple to a $G_i$ protein since it has been associated with inhibition of adenylate cyclase (J. Stoof and J. Kebabian, *Life Sci.* 35:2281 (1984), which is incorporated herein by reference), and indeed, the cloned $D_2$ receptor has been shown to inhibit cAMP accumulation when expressed in the appropriate cell lines (R. Dal Toso et al., *EMBO J.* 8:4025 (1989); P. Albert et al., *J. Biol. Chem.* 265:2098 (1990), both of which are incorporated herein by reference). However, there have been some reports of $D_2$ receptor-mediated alteration of $[Ca^{+2}]_i$ (R. Todd et al., *Proc. Natl. Acad. Sci. USA* 86:10134 (1989); M. Wolf and G. Kapatos, *Synapse* 4:353 (1980), both of which are incorporated herein by reference). When the $D_{2(414)}$ receptor was expressed in CHO cells, dopamine (100 μM) failed to alter $[Ca^{+2}]_i$ (FIG. 3A). Shown in FIG. 3B are the results of calcium studies with the $D_2$/m1 chimeric receptor. $[Ca^{+2}]_i$ was elevated in a dose dependent manner in response to dopamine. This effect of dopamine was blocked by the dopamine antagonist fluphenazine (FIG. 3C).

Specific binding of [$^3$H]-spiperone (0.5 nM) at twelve different concentrations of competing ligand was determined in triplicate. $IC_{50}$'s were determined by analysis with the program ALLFIT (A. De Lean et al., *Am. J. Physiol.* 235:E97 (1978), which is incorporated herein by reference) and $K_i$ computed using the Cheng-Prusoff equation (Y. Cheng and W. Prusoff, *Biochem. Pharmacol.* 22:3099 (1973), which is incorporated herein by reference). $K_d$ values for [$^3$H]-spiperone, which differed between the two receptors, are given in the text. Values are the anti-log of the mean log $K_i$ from three separate experiments and 95% confidence intervals calculated from the standard deviation of the log $K_i$.

While the invention has been described in connection with certain embodiments thereof, it should be recognized that various modifications as may be apparent to one of skill in the art to which the invention pertains also fall within the scope of the invention as defined by the appended claims.

---

What is claimed is:

1. A nucleic acid having a sequence encoding a polypeptide having the amino acid sequence of SEQ. ID NO. 7.

2. A mammalian expression vector comprising a promoter operably linked to a nucleic acid of claim 1.

3. A cell into which has been introduced an expression vector of claim 2.

4. A cell capable of expressing a chimeric G-protein-linked receptor protein, said cell comprising a nucleic acid of claim 1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:1:

CGGAATTCCC AGCCCACCT AGCCACCA 28

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:2:

GGGGATCCGA GGGATGCAGG AGAGGGGAC 29

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:3:

GCGAATTCAT GGATCCACTG AATCTGTCC 29

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:4:

GATAAGCTTC AGCAGTGGAG GATCTTCAG         29

( 2 ) INFORMATION FOR SEQ ID NO:5:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:5:

CTTCATTGTC ACCCTGCTGG TCTACTGGCG CATCTACCGG GAGA     44

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:6:

GAACACGCCG AGAACAATGG CGAGGGTCCG AGCCGCCTTC TTCTC     45

( 2 ) INFORMATION FOR SEQ ID NO:7:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Pro Ala Phe Val Val Tyr Ser Ser Ile Val Ser Phe Tyr Val Pro Phe
1           5               10              15

Ile Val Thr Leu Leu Val Tyr Trp Arg Ile Tyr Arg Glu Thr Glu Glu
        20              25              30

Lys Lys Ala Ala Arg Thr Leu Ala Ile Val Leu Gly Val Phe Ile Ile
        35              40              45

Cys Trp Leu Pro Phe Phe Ile Thr His Ile Leu Asn Ile His
50              55              60